(12) United States Patent
Ries

(10) Patent No.: US 8,449,546 B2
(45) Date of Patent: May 28, 2013

(54) SPINE CUTTER

(75) Inventor: Wolfgang Ries, Linkenheim (DE)

(73) Assignee: Joimax GmbH, Karlsruhe (DE)

( * ) Notice: Subject to any disclaimer, the term of this patent is extended or adjusted under 35 U.S.C. 154(b) by 375 days.

(21) Appl. No.: 12/777,556

(22) Filed: May 11, 2010

(65) Prior Publication Data

US 2010/0292700 A1    Nov. 18, 2010

(30) Foreign Application Priority Data

May 12, 2009    (DE) .................... 20 2009 006 792 U

(51) Int. Cl.
*A61B 17/16*    (2006.01)

(52) U.S. Cl.
USPC ........................................ 606/80

(58) Field of Classification Search
USPC .............. 606/79–85, 86 R; 623/17.11–17.16; 408/204–206
See application file for complete search history.

(56) References Cited

U.S. PATENT DOCUMENTS

| | | | |
|---|---|---|---|
| 749,624 A | | 1/1904 | McCullough |
| 3,609,056 A | * | 9/1971 | Hougen .................. 408/204 |
| 4,452,554 A | * | 6/1984 | Hougen .................. 408/206 |
| 4,559,936 A | * | 12/1985 | Hill ................... 606/79 |
| 5,190,548 A | | 3/1993 | Davis |
| 5,312,408 A | | 5/1994 | Brown |
| 5,505,732 A | * | 4/1996 | Michelson ................. 606/86 A |
| 5,785,522 A | | 7/1998 | Bergstrom et al. |
| 5,899,908 A | * | 5/1999 | Kuslich et al. ................. 606/96 |
| 6,200,322 B1 | * | 3/2001 | Branch et al. .................... 606/96 |
| 6,306,142 B1 | | 10/2001 | Johanson et al. |
| 6,322,564 B1 | | 11/2001 | Surma |
| 6,332,886 B1 | * | 12/2001 | Green et al. .................... 606/80 |
| 6,663,637 B2 | * | 12/2003 | Dixon et al. .................... 606/90 |
| 6,676,711 B2 | * | 1/2004 | Omi .................. 83/847 |
| 6,692,501 B2 | * | 2/2004 | Michelson ...................... 606/80 |
| 6,942,669 B2 | * | 9/2005 | Kurc ............................. 606/80 |
| 2003/0170591 A1 | | 9/2003 | Kurer |
| 2009/0112261 A1 | * | 4/2009 | Barry ...................... 606/246 |

FOREIGN PATENT DOCUMENTS

| | | |
|---|---|---|
| DE | G94 20 565.5 | 2/1995 |
| DE | 29616633 | 11/1996 |
| DE | 69217689 | 7/1997 |
| DE | 202005016763 | 11/2006 |
| GB | 2 164 277 A | 3/1986 |
| WO | WO 93/24061 | 12/1993 |

* cited by examiner

*Primary Examiner* — Kevin T Truong
*Assistant Examiner* — Christopher Beccia
(74) *Attorney, Agent, or Firm* — McGlew and Tuttle, P.C.

(57) ABSTRACT

A cutter for spine surgery is provided, especially for use in the area of the delicate cervical spine. The cutter includes a cylindrical cutter shank with cutter teeth formed at the distal end thereof. The cutter teeth at the distal end of the cutter shank are formed by grooves in the wall of the cutter shank. The grooves become deeper and expand from the outer radius of the cutter shank towards the distal end such that teeth narrowing towards the distal end with increasing height are formed between them. This guarantees especially gentle cutting in the area of the cervical spine, without surrounding delicate tissue being additionally jeopardized.

13 Claims, 2 Drawing Sheets

Fig. 1
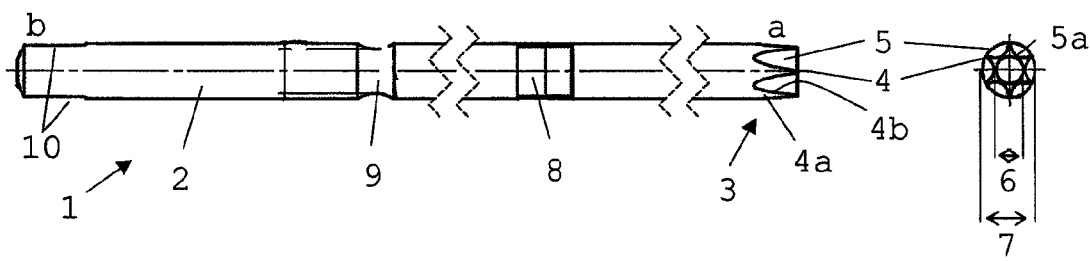
Fig. 1a
Fig. 2
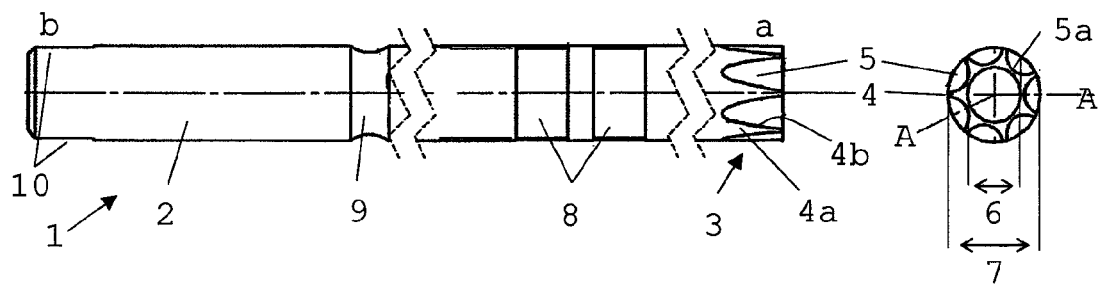
Fig. 2a
Fig. 3
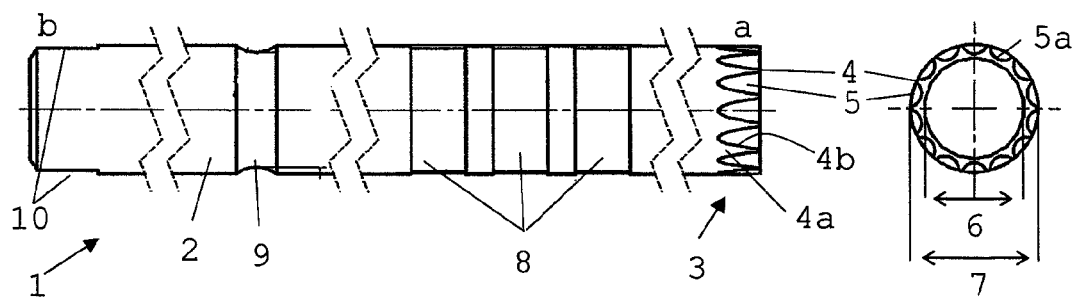
Fig. 3a
Fig. 4
A - A
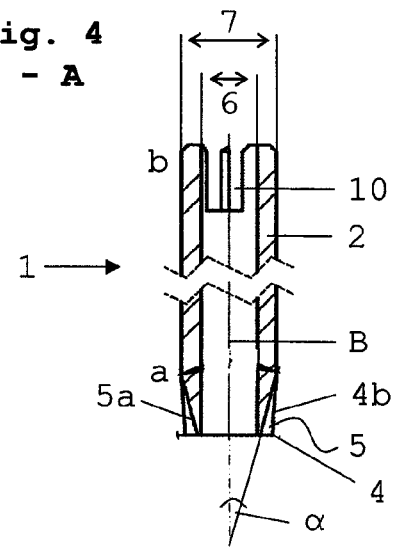

C - C

SPINE CUTTER

CROSS REFERENCE TO RELATED APPLICATIONS

This application claims the benefit of priority under 35 U.S.C. §119 of German Patent Application DE 20 2009 006 792.0 filed May 12, 2009, the entire contents of which are incorporated herein by reference.

FIELD OF THE INVENTION

The present invention pertains to a cutter for spine surgery, especially for use in the area of the cervical spine, with a cylindrical cutter shank and cutter teeth formed at the distal end thereof, as well as with a cutter set comprising the aforementioned cutters.

BACKGROUND OF THE INVENTION

A cutter of this type is known from DE 20 2005 016 763 U1 and describes a facet joint cutter, which is used to cut out vertebral components in the area of the spine. This cutter has a cylindrical shank and sawtooth-like teeth formed at its front-side, distal end. The teeth point forward from the distal end, and said teeth are slightly expanded outwardly. The teeth are directed parallel to the axis, and grooves, which likewise extend parallel to the axis and extend radially from the internal diameter of the cutter wall up to the external diameter, are located between them.

It was found that the bone material cannot be cut out sufficiently gently, especially from the delicate cervical vertebrae, with the prior-art cutters.

SUMMARY OF THE INVENTION

The basic object of the present invention is therefore to create improved cutters for endoscopic spine surgery while avoiding the aforementioned drawbacks.

This object is accomplished with a cutter of the type mentioned in the introduction by the teeth of the cutter at the distal end of the cutter shank being formed by grooves in the wall of the cutter shank, which deepen and expand from the outer radius of the cutter shank towards the distal end such that teeth narrowing towards the distal end with increasing height are formed between them.

Due to the teeth modified compared to the state of the art, which are formed in a star-shaped pattern on the distal front side of the cutter shank such that the front side of the teeth point from the inner wall side of the shank radially outwardly, and especially with a flat front-side closure, wherein the cutting edges are formed at the edge of the front side, more gentle cutting is achieved along with uniform precision and cutting action. The base of the grooves between the teeth, the groove base, is closed; consequently, no slots extending completely radially through the shank wall are formed between the teeth. The tooth flanks extending in the wall of the cylindrical shank are directed outwardly in a star-shaped pattern on the front side. Great sharpness of the teeth of the individual cutters is nevertheless guaranteed.

The teeth are separated by grooves, the grooves cut expand parabolically in the axial direction towards a distal end facing the vertebra to be cut and the teeth have a transition edge corresponding to the shape of the groove between the groove and the tooth wall. The groove bases have an angle of at least 13° to 15° in relation to a longitudinal axis of the cutter. Furthermore, the present invention makes provisions for the teeth defined by tooth walls becoming pointed parallel to the axis and/or for the edges of the tooth walls becoming pointed towards the distal end parallel to the axis, and provisions may also be made for the tooth walls becoming pointed towards the distal end beginning from half of their groove length. Outer edges of the tooth walls are extremely preferably located on an external diameter of the cutter shank, and the cutting edges may also be formed on the front side. This makes possible an especially gentle cutting without surrounding delicate tissue being jeopardized. Such a cutter can be used as a cervical spine cutter especially for the cervical spine. Preferred variants of such a cutter make provisions for outer edges of the teeth to be located on an external diameter of the cutter shank and/or for edges of the tooth walls to become pointed towards the distal end parallel to the axis.

In another preferred embodiment the teeth have bent outer tooth walls, and the tooth walls extend parallel to the axis over up to half the length of the grooves and at an angle of at least 30° in relation to the longitudinal axis of the cutter towards the distal end. Provisions may be made here for the teeth having sharp cutting edges at the obliquely extending transition edges. Thus, sharp cutting edges of the teeth are formed in all embodiments of the cutter at the front-side end or in the obliquely extending area only.

In a preferred embodiment, the shank has at least one or more colored ceramic rings towards a proximal end for better distinction of cutters of different sizes, the heat-resistant ceramic rings being more durable and resistant than colored rings made of plastic.

An annular recess, with which the cutter can be clamped in a corresponding handling or rotating device, is formed on the shank of the cutter according to the present invention, and at least two rectangular slots are formed at a proximal end in another embodiment, and a torque can be transmitted to the cutter due to positive-locking connection with the handling or rotating device.

The cutter preferably has 4 to 8 teeth at an internal diameter of less than 2 mm of its wall, 5 to 10 teeth at an internal diameter of 2 mm to 2.5 mm, 10 to 16 teeth at an internal diameter of 3 mm to 4 mm and 12 to 24 teeth at an internal diameter greater than 5 mm.

A set of cutters, comprising at least three cutters, is preferably provided, wherein a first cutter has an external diameter that corresponds, possibly taking tolerances into account, at most to an internal diameter of a next larger cutter. The external and internal diameters of the cutters are thus very preferably coordinated such that the cutters can be pushed one into the other. At least one cutter of a set of cutters has an external diameter greater than 5 mm.

Other advantages and features appear from the claims and from the following description, in which an exemplary embodiment of the present invention is specifically explained with reference to the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a schematic enlarged view of a first cutter, according to the present invention, with an external diameter of 2 mm;

FIG. 1a is a schematic view of the front side of the cutter according to the present invention from FIG. 1;

FIG. 2 is a schematic enlarged view of another cutter according to the present invention with an external diameter of 3.6 mm;

FIG. 2a is a schematic view of the front side of the cutter according to the present invention from FIG. 2;

FIG. 3 is a schematic enlarged view of another cutter according to the present invention with an external diameter of 4.7 mm;

FIG. 3a is a schematic view of the front side of the cutter according to the present invention from FIG. 3;

FIG. 4 is a schematic sectional view of a cutter according to the present invention in section A-A from FIG. 2a;

DESCRIPTION OF THE PREFERRED EMBODIMENTS

Figure 5:
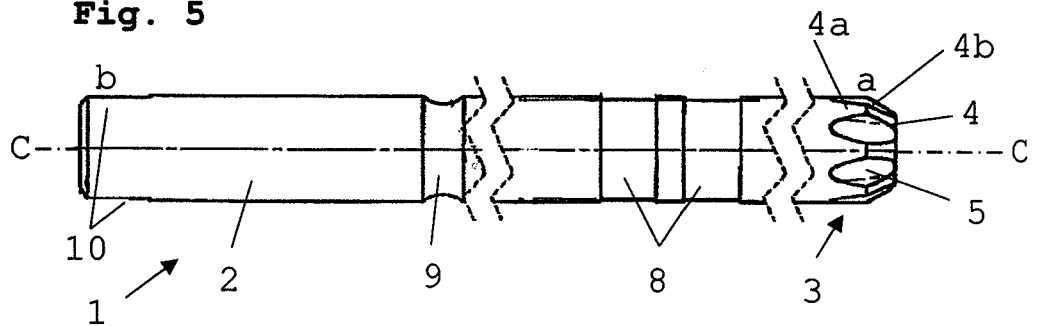
FIG. 5 is a schematic enlarged view of another cutter according to the present invention with another embodiment of the teeth.

Referring to the drawings in particular, FIGS. 1, 2 and 3 show a schematic view each of cutters 1 according to the present invention and the cutters 1 together form a set of cutters 1 of different sizes. Serrated lines in the figures indicate a shortening of the length in the drawing for the sake of greater clarity.

A cutter 1, as it is shown in the exemplary embodiment according to FIG. 1 or FIG. 1a, has a cylindrical shank 2, which is formed from a long steel tube. A front-side, distal end a of cutter 1 is formed as a set of cutter teeth 3, which comprise teeth 4 and grooves 5 located between them. Grooves 5 are cut in the axial direction parabolically into the wall of shank 2, and the grooves 5 expand radially as well as axially towards the distal end a. Thus, they show a partly conical incision in the wall of shank 2. The teeth 4 are formed from the tooth walls 4a left behind after the grooves 5 have been cut out, the tooth walls 4a becoming pointed parallel to the axis towards the distal end a. A transition edge 4b corresponding to the parabolic shape of groove 5 is formed between the tooth wall 4a and the groove 5. Transition edge 4b may have a sharpened edge. Grooves 5 and the adjoining tooth walls 4a thus show an axial direction of the main course parallel to the axis, so that the teeth 4 formed are located on the external diameter of shank 2. Cutter 1 has a flat closure on the front side. This flat closure brings about the formation of a sharp cutting edge of the teeth 4 at the front-side, distal end a. As an alternative, a bent closure may also be provided, which will be explained in more detail below in FIGS. 5 and 5a.

Furthermore, shank 2 of cutter 1 has a recessed colored ceramic ring 8 with a width of about 2 mm. The cutters 1 in FIGS. 2 and 3 have not only a colored ceramic ring 8, but correspondingly two or three colored ceramic rings 8. It is thus possible to distinguish the different cutters by means of the number and color of the ceramic rings 8. Furthermore, shank 2 has an annular recess 9, whose center is located at a distance of 13 mm from a proximal end b located opposite the distal end a in the exemplary embodiment according to FIGS. 1-3 and which is used to axially fasten the cutter 1 in a corresponding handling or rotating device.

The set of cutter teeth 3 are shown, furthermore, in a schematic front view in FIGS. 1a, 2a and 3a for the respective sizes of the cutters 1, showing that the teeth 4 are shaped radially outwardly, i.e., in a star-shaped pattern, in one plane on the cutter head due to the correspondingly cut grooves 5 and the flat closure at the distal end a. In the front-side view, the grooves 5 cut point-symmetrical as circle segments towards the center of the front-side radial plane have a certain depth 5, which is defined by a thin wall to an internal diameter 6. The teeth 4 are arranged each at right angles to the circumference of the cutter head, and their outer edges are located on an external diameter 7 of shank 2. The outer edges are defined by the pointed transition edge 4b, as a result of which a sharp outer cutting edge of teeth 4 is obtained at the front-side distal end a.

FIG. 4 shows a longitudinal section through cutter 1 through the connection A-A in FIG. 2a. Furthermore, the distal end a with the set of teeth 3 with teeth 4 and grooves 5 is again shown in FIG. 4 in a longitudinal section by a shortening of the drawing, the grooves 5 having a groove base 5a. Groove base 5a changes here over the length of the grooves 5 radially with the axial height at a certain angle α towards a longitudinal axis B and ends on the front side at the distal end a. This angle α equals approx. 15° for the cutters 1 from FIGS. 1 and 2 and the angle α equals approx. 13° for cutter 1 from FIG. 3. It can be clearly recognized here that the teeth 4 are located on the external diameter 7 of shank 2.

Furthermore, at least two opposite rectangular slots 10, by means of which a torque can be transmitted to the cutter 1 by positive-locking connection with a corresponding handling or rotating device, are formed at the proximal end b of shank 2.

Figure 5A:
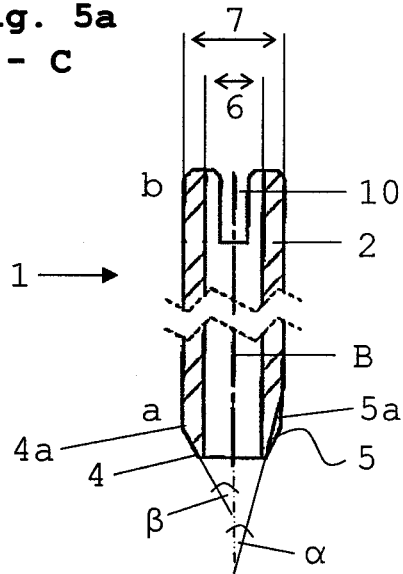
FIG. 5a is a schematic sectional view of a cutter according to the present invention in sectional view C-C from FIG. 5.

FIGS. 5 and 5a show an alternative embodiment of the teeth of cutter 1 according to the present invention with a bent closure at the distal end a. The teeth are again formed by grooves 5 cut parabolically in the wall of cutter 1 in the axial direction, wherein the tooth walls 4a formed hereby are at first parallel to the axis towards the distal end a. Beginning from half the length of the grooves 5, the tooth walls 4a are bent radially inwardly. The groove bases 5a are made pointed towards the distal end a, and the tooth walls 4a have a nearly constant width. Due to the flat front-side closure, a sharp cutting edge is obtained directly on the front side. An additional cutting edge may be formed in the obliquely extending area of the tooth walls 4a.

FIG. 5a shows for this a longitudinal section according to section C-C, with shortening of the drawing for the sake of greater clarity, through the cutter 1 in FIG. 5. For the variant of the teeth 3 being shown here, the groove base 5a of the grooves 5 likewise varies radially with the axial height with the angle α towards the longitudinal axis B and ends on the front side at the distal end a. As was already described in FIG. 5, the tooth walls 4a do not extend parallel to the axis over their entire length, but are bent beginning from half of the length of groove 5 at an angle β towards the longitudinal axis B of cutter 1 and likewise end at the distal end a on the front side. This variant of the teeth 3 has values of α=13°-15° and β=30°.

In this exemplary embodiment the cutters 1 according to FIGS. 1-3 cover, furthermore, as a set of cutters the following dimensions of the internal diameter 6, external diameter 7, number of teeth 4 and overall length of the cutter 1:

| Internal diameter 6 [mm] | External diameter 7 [mm] | Number of teeth 4 | Overall length of cutter 1 [mm] |
|---|---|---|---|
| 1 | 2 | 6 | 250 |
| 2.1 | 3.6 | 7 | 230 |
| 3.7 | 4.7 | 14 | 210 |

The cutters 1 from FIGS. 1 and 3 have a wall with a thickness of about 0.5 mm. The cutter in FIG. 2 has for this a wall thickness of about 0.75 mm. Besides the dimensions listed here, cutters 1 with an external diameter 7 greater than 5 mm with up to 24 teeth are also provided with the corresponding other dimensions adapted hereto.

Due to the diameters coordinated with one another, in which the external diameter 7 of a thin cutter 1 fits the internal diameter 6 of the next thicker cutter 1 with a tolerance of 0.1 mm, the cutters 1 as a set of cutters can be optimally pushed one into the other, so that they can be placed for this one over another and/or split up for hollowing out in a vertebra. They can be distinguished in their different sizes not only by the different external diameters 7, but also by the different number of colored ceramic rings 8 consisting of heat-resistant ceramic. Common to all is the annular recess 9 and the rectangular slot 10 at the proximal end b of shank 2, which make it possible to firmly clamp the cutters 1 in a corresponding handling or rotating device and to transmit a torque due to positive-locking connection with the handling or rotating device, as a result of which precise operation is made possible in endoscopic spine surgery.

While specific embodiments of the invention have been described in detail to illustrate the application of the principles of the invention, it will be understood that the invention may be embodied otherwise without departing from such principles.

What is claimed is:

1. A set of at least three cutters, each of the at least three cutters comprising:
a cylindrical cutter shank with a cylindrical wall and an inner circumferential inner surface, said cylindrical wall having a continuous outer cylindrical wall surface and a longitudinal axis, said outer cylindrical wall surface defining a plurality of outer radial extents and a plurality of inner radial extents at a distal end of said shank, said outer radial extents defining a plurality of teeth of said cylindrical wall, said outer radial extents and said inner radial extents defining a plurality of grooves in said cylindrical wall, each of said grooves being located between one of said outer radial extents and another one of said outer radial extents, each of said outer radial extents being located at a position that is radially outward of one or more of said inner radial extents, each of said outer radial extents extending from an outer radial extent position to said distal end, said outer radial extent position being located at a spaced location from said distal end, each of said inner radial extents extending from an inner radial extent position to said distal end, said inner radial position being located at a spaced location from said distal end, wherein a thickness of each of said inner radial extents decreases from said inner radial extent position to said distal end with respect to the longitudinal axis and a width of each of said outer radial extents decreases from said outer radial extent position to said distal end with respect to the longitudinal axis, whereby a depth of said grooves increases towards the distal end with respect to the longitudinal axis and a distance between each of said outer radial extents and another one of said outer radial extents increases from said outer radial extent position to said distal end, wherein a first cutter has an external diameter that corresponds at most to an internal diameter of a next larger second cutter and the second cutter has an external diameter that corresponds at most to an internal diameter of a further larger third cutter whereby the cutters can be pushed one into the other.

2. A spine cutter in accordance with claim 1, wherein each of said teeth extends parallel to said longitudinal axis.

3. A spine cutter in accordance with claim 1, wherein outer tooth walls extend parallel in relation to said longitudinal axis up to half a length of the grooves and a cutting edge of the teeth extends at an angle of at least 30° in relation to said longitudinal axis towards the distal end.

4. A spine cutter in accordance with claim 3, wherein tooth flanks become pointed beginning from half the length of the grooves towards the distal end.

5. A spine cutter in accordance with claim 1, wherein the teeth have sharp cutting edges at obliquely extending transition edges.

6. A spine cutter in accordance with claim 1, wherein the cylindrical cutter shank has at least one or more colored ceramic rings towards a proximal end for marking the cylindrical cutter shank for distinction of cutters of different sizes.

7. A spine cutter in accordance with claim 1, wherein an annular recess is formed on the cylindrical cutter shank for fastening the cylindrical cutter shank in a handling or rotating device and at least two opposite rectangular slots are formed at a proximal end of the cylindrical cutter shank, wherein a torque can be transmitted to the cylindrical cutter shank by positive-locking connection of the cylindrical cutter shank with the handling or rotating device, said inner circumferential inner surface defining a hollow space at said distal end.

8. A spine cutter in accordance with claim 1, wherein the teeth extend parallel in relation to said longitudinal axis.

9. A set of cutters in accordance with claim 1, wherein
the first cutter has an internal diameter of 1 mm and an external diameter of 2 mm;
the second cutter has an internal diameter of 2.1 mm and an external diameter of 3.6 mm; and
the third cutter has an internal diameter of 3.7 mm and an external diameter of 4.7 mm.

10. A set of cutters in accordance with claim 1, wherein each of the grooves expand, in an axial direction with respect to said longitudinal axis, parabolically towards the distal end, each of said outer radial extents being located at a distance from said longitudinal axis that is greater than a distance between each of said inner radial extents and said longitudinal axis, each of said outer radial extents extending parallel to said longitudinal axis.

11. A set of cutters in accordance with claim 1, wherein said cutter teeth have a transition edge corresponding to a groove shape between at least one of the grooves and a tooth wall.

12. A set of cutters in accordance with claim 1, wherein groove bases of said grooves have an angle of at least 13°-15° in relation to said longitudinal axis of each cutter.

13. A spine cutter in accordance with claim 1, wherein front-side distal cutting edges of said outer radial extents are located in a radial plane.

* * * * *